(12) United States Patent
Campain

(10) Patent No.: US 7,744,859 B2
(45) Date of Patent: Jun. 29, 2010

(54) SEMIPERMANENT HAIR SHAPING METHOD

(75) Inventor: Catherine Campain, Paris (FR)

(73) Assignee: L'Oreal S.A., Paris (FR)

( * ) Notice: Subject to any disclaimer, the term of this patent is extended or adjusted under 35 U.S.C. 154(b) by 918 days.

(21) Appl. No.: 11/414,191

(22) Filed: May 1, 2006

(65) Prior Publication Data

US 2006/0260632 A1 Nov. 23, 2006

Related U.S. Application Data

(60) Provisional application No. 60/726,210, filed on Oct. 14, 2005.

(30) Foreign Application Priority Data

Apr. 29, 2005 (FR) .................................. 05 51133

(51) Int. Cl.
*A61Q 5/06* (2006.01)

(52) U.S. Cl. ............... 424/70.11; 424/70.12; 424/70.16

(58) Field of Classification Search ........................ None
See application file for complete search history.

(56) References Cited

U.S. PATENT DOCUMENTS

| | | | |
|---|---|---|---|
| 2,047,398 A | 7/1936 | Voss et al. | |
| 2,723,248 A | 11/1955 | Wright | |
| 3,579,629 A | 5/1971 | Pasero et al. | |
| 3,716,633 A | 2/1973 | Viout et al. | |
| 3,810,977 A | 5/1974 | Levine et al. | |
| 3,836,537 A | 9/1974 | Boerwinkle et al. | |
| 3,925,542 A | 12/1975 | Viout et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,049,007 A * | 9/1977 | Russell et al. ............... | 132/203 |
| 4,070,533 A | 1/1978 | Papantoniou et al. | |
| 4,076,912 A | 2/1978 | Papantoniou et al. | |
| 4,128,631 A | 12/1978 | Lundmark et al. | |
| 4,129,711 A | 12/1978 | Viout et al. | |
| 4,137,208 A | 1/1979 | Elliott | |
| 4,217,914 A | 8/1980 | Jacquet et al. | |
| 4,240,450 A * | 12/1980 | Grollier et al. ............... | 132/209 |
| 4,282,203 A | 8/1981 | Jacquet et al. | |
| 4,348,202 A | 9/1982 | Grollier et al. | |
| 4,366,827 A | 1/1983 | Madrange et al. | |
| 4,422,853 A | 12/1983 | Jacquet et al. | |
| 4,579,732 A | 4/1986 | Grollier et al. | |
| 4,660,580 A | 4/1987 | Hoch et al. | |
| 4,693,935 A | 9/1987 | Mazurek | |
| 4,728,571 A | 3/1988 | Clemens et al. | |
| 4,777,040 A | 10/1988 | Grollier et al. | |
| 4,948,579 A | 8/1990 | Jacquet et al. | |
| 4,970,066 A | 11/1990 | Grollier et al. | |
| 4,972,037 A | 11/1990 | Garbe et al. | |
| 5,196,189 A | 3/1993 | Jacquet et al. | |
| 5,225,191 A | 7/1993 | de Labbey | |
| 6,471,953 B1 | 10/2002 | N'Guyen et al. | |
| 6,964,774 B1 * | 11/2005 | Dieing et al. ............... | 424/401 |
| 2005/0074418 A1 | 4/2005 | Campain et al. | |

FOREIGN PATENT DOCUMENTS

| | | | |
|---|---|---|---|
| DE | 23 30 956 | | 1/1974 |
| EP | 0 412 704 | | 2/1991 |
| EP | 0 412 707 | | 2/1991 |
| EP | 0 582 152 | | 2/1994 |
| EP | 1 064 921 | | 1/2001 |
| EP | 1 506 768 | | 2/2005 |
| FR | 1 222 944 | | 6/1960 |
| FR | 1 400 366 | | 5/1965 |
| FR | 1 564 110 | | 4/1969 |
| FR | 1 580 545 | | 9/1969 |
| FR | 2245339 | * | 4/1975 |
| FR | 2 265 782 | | 10/1975 |
| FR | 2 350 384 | | 12/1977 |
| FR | 2 439 798 | | 5/1980 |
| FR | 2 465 478 | | 3/1981 |
| FR | 2 495 931 | | 6/1982 |
| GB | 839 805 | | 6/1960 |
| GB | 922 457 | | 4/1963 |
| GB | 1 021 400 | | 3/1966 |
| GB | 2 025 228 | | 1/1980 |
| GB | 1 572 555 | | 7/1980 |
| GB | 1 572 626 | | 7/1980 |

(Continued)

OTHER PUBLICATIONS

English language Derwent abstract for FR 2 245 339.
English language Derwent abstract for FR 2 357 241.
English language Derwent abstract for FR 2 514 640.
English language Derwent abstract for WO 2005/087186.
French Search Report for FR 05/51133 dated Dec. 9, 2005 (corresponding to the present application).

*Primary Examiner*—Jyothsna A Venkat
(74) *Attorney, Agent, or Firm*—Finnegan, Henderson, Farabow, Garrett & Dunner, L.L.P.

(57) ABSTRACT

Disclosed herein is a semipermanent hair shaping method comprising:
(a) applying onto the hair a first composition comprising, in a cosmetically acceptable medium, at least one solubilized fixing polymer chosen from anionic and amphoteric polymers, this application being optionally followed by a resting time for said first composition,
(b) applying onto the hair a second composition comprising in a cosmetically acceptable medium at least one acid chosen from mineral and organic acids, such application being optionally followed by a resting time for said second composition,
where step b) is conducted prior to or after step a),
(c) rinsing the hair, and
(d) shaping the hair either after applying the first composition of step a), or after applying the second composition of step b) and prior to the rinsing step c).

3 Claims, No Drawings

FOREIGN PATENT DOCUMENTS

| | | |
|---|---|---|
| LU | 75370 | 2/1978 |
| LU | 75371 | 2/1978 |
| WO | WO 93/23009 | 11/1993 |
| WO | WO 93/23446 | 11/1993 |
| WO | WO 95/00578 | 1/1995 |
| WO | WO 95/03776 | 2/1995 |

* cited by examiner

SEMIPERMANENT HAIR SHAPING METHOD

This application claims benefit of U.S. Provisional Application No. 60/726,210, filed Oct. 14, 2005, the contents of which are incorporated herein by reference. This application also claims benefit of priority under 35 U.S.C. §119 to French Patent Application No. 05 51133, filed Apr. 29, 2005, the contents of which are also incorporated herein by reference.

Disclosed herein is a method for shaping the hair.

Conventionally, two main classes of products are used for shaping the hair: hair styling products and permanenting products.

The styling products make it possible to reshape the hair non-permanently. Typically, they may be used on wet or dry hair prior to being shaped with the hand, with a brush, and/or with a comb. After their application onto the hair, and once they have been dried, these products may substantially harden. This hardening creates a texturized and dry feel that is necessary for retaining and volumizing the hair style. However, such styling products are typically washed out after a shampoo and hence have to be applied every day.

Permanenting products enable a longer lasting hair shaping. Traditionally, the practice used to obtain a permanent reshaping of the hair comprises opening the keratin —S—S— disulfide bonds (cystine) by applying to hair which has been placed beforehand under tension (with rollers or equivalent suitable means) a reducing composition (reducing step), then, after optionally rinsing the treated hair, re-forming said disulfide bonds by applying to the hair still remaining under tension an oxidizing composition (oxidizing step, also called fixing step) so as to finally give to the hair the desired form.

The new shape that has been imposed on the hair by means of a chemical treatment as described above is typically longer lasting and more resistant to the effect of washing with water and/or shampoos.

However, such a method is not always fully satisfactory. While it is indeed very efficient to reshape the hair, it may cause great damage to the hair fibers.

There is, therefore, a need for a method that is fast and easy to use, that is not damaging to the hair, and/or that provides the hair with a good hold while being remanent with respect to shampoo, and wherein the hair to which this method is applied has at least one good cosmetic quality chosen, for example, from softness, shine, and a non-sticky feel. When such a method is used, shine and feel properties may be improved as compared to a styling product, and fiber integrity and color may be improved as compared to a permanenting product.

A two-part fixing product is described in French Patent No. 2 245 339, to be applied simultaneously or consecutively, the first part being an alkaline silicate or an aluminum salt-containing solution, and the second part being a solution comprising a polymer used at an acidic or alkaline pH value. These two solutions, by interacting with each other, result in a silicic acid or aluminum hydrate-based precipitate, which is deposited onto the hair.

A hair treating composition is also described in British Patent No. 2 025 228, comprising a mixture of a cationic polymer and an anionic polymer, said cationic and anionic polymers being suitable for producing a complex that will precipitate on the hair in the presence of a calcium salt.

However, neither system provides sufficient cosmetic properties and/or durability of the resulting effect.

Therefore, to solve at least one of the above-mentioned drawbacks, disclosed herein is a hair shaping method comprising:

(a) applying to the hair a first composition comprising, in a cosmetically acceptable medium, at least one solubilized fixing polymer chosen from anionic and amphoteric polymers, this application optionally being followed by a resting time for said first composition, (b) applying to the hair a second composition comprising, in a cosmetically acceptable medium, at least one acid chosen from mineral and organic acids, such application optionally being followed by a resting time for said second composition, where step b) may be conducted prior to or after step a), (c) rinsing the hair, and (d) shaping the hair either after applying the first composition of step a), or after applying the second composition of step b) and prior to the rinsing step c).

The resting time for the first or the second composition may occur at room temperature or by heating at a temperature ranging from 30 to 250 C, such heating being provided by a hair drier, a hood, a straightening iron, a curling iron, by means of a steam generating device, and/or by means of an IR generating device.

The thus-obtained hair shape is remanent with respect to at least one shampoo, for example, with respect to at least two shampoos.

According to one embodiment, the method of the present disclosure does not comprise any step comprising opening the hair keratin disulfide bonds by means of a reducing composition, or any step comprising re-forming said disulfide bonds by means of an oxidizing composition.

Fixing Polymers

As used herein, the term "fixing polymer" means any polymer that can give the hair a shape or that can modify the shape of said hair.

As described above, the first composition comprises at least one fixing polymer chosen from anionic and amphoteric polymers.

Anionic Fixing Polymers

The anionic polymers which may be used in accordance with the present disclosure include, but are not limited to, polymers comprising at least one group derived from an acid chosen from carboxylic, sulfonic, and phosphoric acids and having a weight-average molecular weight ranging from 500 to 5 000 000.

Carboxylic moieties may be provided, for example, by at least one monomer chosen from unsaturated, carboxylic, monoacidic, and diacidic monomers, such as those of formula (I):

wherein:

n is an integer ranging from 0 to 10,

A is a methylene moiety, optionally bound to the carbon atom of the unsaturated moiety or to the adjacent methylene moiety when n is more than 1, through a heteroatom, such as, for example, oxygen and sulfur, $R_1$ is chosen from hydrogen, phenyl moieties, and benzyl moieties, $R_2$ is chosen from hydrogen, lower alkyl moieties, and carboxyl moieties, and $R_3$ is chosen from hydrogen, lower alkyl moieties, —$CH_2$—COOH, phenyl moieties, and benzyl moieties.

In the above formula (I), a lower alkyl moiety may comprise from 1 to 4 carbon atoms and may, in at least one embodiment, be chosen from methyl and ethyl moieties.

Non-limiting examples of carboxylic or sulfonic moiety-containing anionic polymers according to the present disclosure include:

A) Homo- or copolymers of acrylic or methacrylic acid and salts thereof, including copolymers of acrylic acid and acrylamide and copolymers of methacrylic acid and acrylic acid/ethyl acrylate/methyl methacrylate, for example, AMERHOLD DR25 marketed by AMERCHOL and sodium salts of polyhydroxycarboxylic acids. Copolymers of methacrylic acid/ethyl acrylate in aqueous dispersion, such as LUVIFLEX SOFT and LUVIMER MAE marketed by BASF are also suitable.

B) Acrylic or methacrylic acid copolymers with a monoethylene monomer such as ethylene, styrene, vinyl esters, acrylic, and methacrylic acid esters, optionally grafted to a polyalkylene glycol such as polyethylene glycol, and optionally crosslinked. Such polymers are described, for example, in French Patent No. 1 222 944 and German Patent Application No. °23 30 956, copolymers of this type comprising in their chain an optionally N-alkylated and/or hydroxyalkylated acrylamide unit, such as described, for example, in Luxembourg Patent Application Nos. 75370 and 75371. Copolymers of acrylic acid and $C_1$-$C_4$ alkyl methacrylate are also suitable.

C) Copolymers derived from crotonic acid such as those comprising at least one unit in their chain chosen from vinyl acetate and vinyl propionate units and optionally other monomers such as allyl and methallyl esters, vinyl ethers and vinyl esters of a saturated, linear, or branched carboxylic acid with a long hydrocarbon chain, such as those comprising at least 5 carbon atoms, where such polymers may be optionally grafted and crosslinked, and a vinyl, allyl, or methallyl ester of an α or β-cyclic carboxylic acid. Such polymers are described, for example, in French Patent Nos. 1°222°944, 1°580°545, 2°265°782, 2°265°781, 1°564°110, and 2°439°798. Commercial products belonging to this class include, for example, 28-29-30 resins, 26-13-14 resins, and 28-13-10 resins marketed by NATIONAL STARCH.

Other examples of crotonic acid derived copolymers include, for example, terpolymers of crotonic acid, vinyl acetate, and vinyl tert-butylbenzoate, for example, MEXOMERE PW marketed by CHIMEX.

D) polymers derived from maleic, fumaric, or itaconic acids or anhydrides with vinyl esters, vinyl ethers, vinyl halides, phenyl vinyl derivatives, acrylic acid and esters thereof, these polymers optionally being esterified. Such polymers are described, for example, in U.S. Pat. Nos. 2,047,398, 2,723,248, and 2,102,113 and British Patent No. 839 805, and are marketed, for instance, under the trade names GANTREZ® AN and ES by ISP.

Additional non-limiting examples of polymers belonging to this class include copolymers of maleic, citraconic, or itaconic anhydride and an allyl or methallyl ester, optionally comprising in their chain at least one entity chosen from acrylamide, methacrylamide, α-olefins, acrylic or methacrylic esters, acrylic or methacrylic acids, and vinyl pyrrolidone, the anhydride functionalities being monoesterified or monoamidified. These polymers are described, for example, in the French Patent Nos. 2 350 384 and 2 357 241.

E) Polyacrylamides comprising carboxylate moieties.

F) Polymers comprising sulfonic moieties. These polymers may be polymers comprising at least one unit chosen from vinyl sulfonic, styrene-sulfonic, naphthalene-sulfonic, acrylamido-alkyl sulfonic, and sulfoisophthalate units.

These polymers may be chosen, for example, from:

polyvinylsulfonic acid salts having a molecular weight ranging from 1 000 to 100 000, as well as copolymers with an unsaturated comonomer such as acrylic or methacrylic acids and esters thereof, acrylamide and derivatives thereof, vinyl ethers, and vinyl pyrrolidone;

polystyrene-sulfonic acid salts, sodium salts, having a molecular weight ranging from 500 000 to 100 000. These compounds are described, for example, in French Patent No. 2 198 719; and polyacrylamide-sulfonic acid salts such as those mentioned in U.S. Pat. No. 4,128,631;

G) Anionic Silicone Graft Polymers:

Silicone graft polymers suitable for use in accordance with the present disclosure may be chosen, for example, from polymers having an organic non-silicone backbone grafted with monomers comprising a polysiloxane, polymers having a polysiloxane backbone grafted with non-silicone organic monomers, and mixtures thereof.

As used herein, the terms "silicone" and "polysiloxane" are intended to mean any oligomeric organosilicone polymer of variable molecular weight having a linear or cyclic, branched or crosslinked structure, obtained by polymerization and/or polycondensation of silanes suitably functionalized and substantially comprising repeating main units wherein silicon atoms are bound with each other through oxygen atoms (siloxane bond ≡Si—O—Si≡), optionally substituted hydrocarbon radicals being directly bound through a carbon atom on said silicon atoms. Examples of common hydrocarbon radicals include alkyl radicals, for instance, $C_1$-$C_{10}$ alkyl radicals, such as methyl; fluoralkyl; aryl radicals such as phenyl radicals; and alkenyl radicals such as vinyl radicals. Other types of radicals that may be bound to the siloxane chain either directly or through a hydrocarbon radical include, but are not limited to, hydrogen; halogens such as chlorine, bromine, and fluorine; thiols; alkoxy radicals; polyoxyalkylene radicals (or polyethers) such as polyoxyethylene and/or polyoxypropylene radicals; hydroxyl radicals; hydroxyalkyl radicals; substituted or unsubstituted amine moieties; amide moieties; acyloxy radicals; acyloxyalkyl radicals; hydroxyalkylamino radicals; aminoalkyl radicals; quaternary ammonium moieties; amphoteric or betaine moieties; anionic moieties such as carboxylates, thioglycolates, sulfosuccinates, thiosulfates, phosphates, and sulfates. These compounds may also include silicones that are said to be "organomodified."

As used herein, the term "polysiloxane macromer" is intended to mean any monomer having in its structure a polysiloxane type polymer chain.

In one embodiment, polymers with an organic non-silicone backbone, grafted with monomers comprising a polysiloxane used according to the present disclosure comprise an organic main chain formed from organic monomers with no silicone, on which at least one polysiloxane macromer is grafted, within said chain as well as optionally on at least one end thereof.

Non-silicone organic monomers comprising the main chain of the graft silicone polymer may be chosen, for example, from ethylenically unsaturated monomers that may be free-radical polymerized, polycondensation polymerizable monomers such as those forming polyamides, polyesters, and polyurethanes, and ring opening monomers such as those of the oxazoline and caprolactone type.

Polymers with a non-silicone organic backbone grafted with monomers comprising a polysiloxane in accordance with the present disclosure may be obtained by any method known in the art, for example, by producing a reaction between (i) a starting polysiloxane macromer suitably functionalized on the polysiloxane chain, and (ii) at least one organic, non-silicone compound that is suitably functionalized with a functionality which can react with the at least one functional moiety carried by said silicone by forming a covalent bond; a traditional example of such a reaction is the free-radical reaction of a vinyl moiety carried on one end of the silicone with a double bond of a main chain ethylenically unsaturated monomer.

Polymers with a non-silicone organic backbone grafted with monomers comprising a polysiloxane in accordance with the present disclosure may be chosen, for example, from those described in U.S. Pat. Nos. 4,693,935, 4,728,571, and 4,972,037, European Patent Application Nos. 0 412 704, 0 412 707, and 0 640 105, and International Patent Application Publication No. WO 95/00578. Copolymers obtained by free-radical polymerization from ethylenically unsaturated monomers and from silicone macromers having a vinyl terminal group, or copolymers obtained by reacting a polyolefin comprising functionalized groups with a polysiloxane macromer having a terminal functionality reactive towards said functionalized groups are also suitable for use.

Another graft silicone polymer family suitable for use in accordance with the present disclosure includes silicone graft copolymers comprising:
a) from 0 to 98% by weight of at least one lipophilic, weakly polar, ethylenically unsaturated, free-radical polymerizable monomer (A);
b) from 1 to 98% by weight of at least one hydrophilic, polar, ethylenically unsaturated monomer (B), copolymerizable with the at least one monomer of type (A); and
c) from 0.01 to 50% by weight of at least one polysiloxane macromer (C) of formula (II):

wherein:
X is a vinyl group that is copolymerizable with monomers (A) and (B);
Y is a divalent binding group;
R is chosen from hydrogen, $C_1$-$C_6$ alkyl groups, $C_1$-$C_6$ alkoxy groups, and $C_6$-$C_{12}$ aryl groups;
Z is a monovalent polysiloxane unit having a number average molecular weight of at least 500;
n is equal to 0 or 1, and
m is an integer ranging from 1 to 3;

the percentages being expressed as compared to the total weight of monomers (A), (B), and (C).

These polymers are described together with their preparation methods, for example, in U.S. Pat. Nos. 4,963,935, 4,728,571, and 4,972,037 and European Patent Application Nos. 0 412 704, 0 412 707, 0 640 105. They have a number average molecular weight ranging, for example, from 10 000 to 2 000 000, and a glass transition temperature or a crystal fusion temperature Tm, for example, of at least −20° C.

Non-limiting examples of suitable lipophilic monomers (A) include acrylic or methacrylic acid esters of $C_1$-$C_{18}$ alcohols; styrene; polystyrene macromers; vinyl acetate; vinyl propionate; α-methyl styrene; tert-butyl styrene; butadiene; cyclohexadiene; ethylene; propylene; vinyl toluene; esters of acrylic or methacrylic acid and 1,1-dihydroperfluoroalkanol and homologs thereof; esters of acrylic or methacrylic acid and ω-hydridofluoroalkanol; esters of acrylic or methacrylic acid and fluoroalkyl sulfoamido-alcohol; esters of acrylic or methacrylic acid and fluoroalkyl alcohol; esters of acrylic or methacrylic acid and fluorether alcohol; and mixtures thereof.

In at least one embodiment, the monomers (A) may be chosen, for example, from n-butyl methacrylate, isobutyl methacrylate, tert-butyl acrylate and methacrylate, 2-ethyl hexyl methacrylate, methyl methacrylate, 2-(N-methyl perfluoroctane sulfoamido)ethyl acrylate; 2-(N-butyl perfluoroctane sulfoamido)ethylacrylate; and mixtures thereof.

Examples of suitable polar monomers (B) include, but are not limited to, acrylic acid, methacrylic acid, N,N-dimethyl acrylamide, dimethylaminoethyl methacrylate, quaternized dimethylaminoethyl methacrylate, (meth)acrylamide, N-t-butyl acrylamide, maleic acid, maleic anhydride and half-esters thereof, hydroxyalkylated (meth)acrylates, diallyl dimethyl ammonium chloride, vinyl pyrrolidone, vinyl ethers, maleimides, vinyl pyridine, vinylimidazole, heterocyclic vinyl polar compounds, styrene sulfonate, allyl alcohol, vinyl alcohol, vinyl caprolactame, and mixtures thereof. In at least one embodiment, the monomers (B) may be chosen from acrylic acid, N,N-dimethyl acrylamide, dimethyl aminoethyl methacrylate, quaternized dimethyl aminoethyl methacrylate, vinyl pyrrolidone, and mixtures thereof.

As polar monomers (B), anionic graft silicone polymers used according to the present disclosure may comprise at least one anionic monomer.

Non-limiting examples of polysiloxane macromers (C) of formula (II) include those of formula (III):

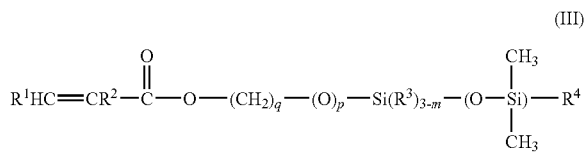

wherein:
$R^1$ is chosen from hydrogen and —COOH, and in at least one embodiment is hydrogen;
$R^2$ is chosen from hydrogen, methyl, and —CH$_2$COOH and in at least one embodiment is methyl;
$R^3$ is chosen from $C_1$-$C_6$ alkyl groups, alkoxy groups, alkylamino groups, $C_1$-$C_{12}$ aryl groups, and hydroxyl groups and in at least one embodiment is methyl;
$R^4$ is chosen from $C_1$-$C_6$ alkyl groups, alkoxy groups, and alkylamino groups, $C_1$-$C_{12}$, aryl groups, and hydroxyl groups and in at least one embodiment is methyl;
q is an integer ranging from 2 to 6 and in at least one embodiment q is 3;
p is equal to 0 or 1;
r is an integer ranging from 5 to 700; and
m is an integer ranging from 1 to 3 and in at least one embodiment, m is 1.

Polysiloxane macromers of formula (IV) may also be used:

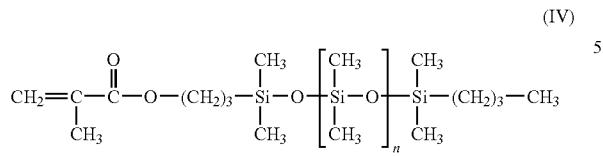

(IV)

wherein n is an integer ranging from 5 to 700.

In one embodiment of the present disclosure, the at least one fixing polymer is a copolymer that may be obtained by free-radical polymerization from a mixture of monomers comprising:
a) 60% by weight of tert-butyl acrylate;
b) 20% by weight of acrylic acid; and
c) 20% by weight of silicone macromer of formula (V):

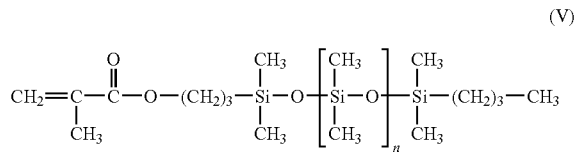

(V)

wherein n is an integer ranging from 5 to 700 and the weight percentages are expressed as compared to the total weight of the monomers.

Further examples of suitable fixing polymers include silicone graft copolymers that may be obtained by a reactive extrusion of a polysiloxane macromer having a reactive end functionality on an olefin type-polymer comprising reactive groups that may react with the polysiloxane macromer end functionality to form a covalent bond, making it possible to graft the silicone on the polyolefin main chain. These polymers together with their production methods are described, for example, in International Patent Application Publication No. WO 95/00578.

Reactive polyolefins may be chosen from polyethylenes and polymers of ethylene-derived monomers such as propylene, styrene, alkyl styrenes, butylene, butadiene, (meth)acrylates, vinyl esters, and equivalents, comprising reactive functionalities that may react with the polysiloxane macromer end functionality. In at least one embodiment, the reactive polyolefins may be chosen from copolymers of ethylene or ethylene derivatives and of monomers chosen from those comprising a carboxyl functionality, such as (meth)acrylic acid; those comprising an acid anhydride functionality such as maleic acid anhydride; those comprising an acid chloride functionality, such as (meth)acrylic acid chloride; those comprising an ester functionality, such as (meth)acrylic acid esters; and those comprising an isocyanate functionality.

Silicone macromers may be chosen, for example, from polysiloxanes comprising a functionalized group at the end of the polysiloxane chain or close to said chain end, chosen from alcohols, thiols, epoxies, primary amines, and secondary amines, for example, macromers of formula (VI):

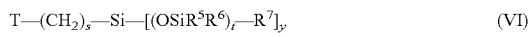

(VI)

wherein:
T is chosen from $NH_2$, NHR', an epoxy functionality, OH, and SH;

$R^5$, $R^6$, $R^7$, and R', which may be identical or different, are independently chosen from $C_1$-$C_6$ alkyl, phenyl, benzyl, and $C_6$-$C_{12}$ alkyl phenyl groups, and hydrogen;
s is a number ranging from 2 to 100;
t is a number ranging from 0 to 1000; and
y is a number ranging from 1 to 3. These macromers have a number average molecular weight ranging, for example, from 5 000 to 300 000, for example, from 8 000 to 200 000, or from 9 000 to 40 000.

According to one embodiment of the present disclosure, the at least one graft silicone polymer having a polysiloxane backbone grafted with non-silicone organic monomers comprises a silicone main chain (or polysiloxane ($\equiv$Si—O—)$_n$) on which at least one organic moiety with no silicone is grafted within said chain as well as optionally on at least one end thereof.

Polymers having a polysiloxane backbone grafted with non-silicone organic monomers of the present disclosure may include existing commercial products or may also be obtained by any method known to one skilled in the art, for example, by conducting a reaction between (i) a starting silicone that is suitably functionalized on at least one of such silicon atoms and (ii) a non-silicone organic compound that itself is suitably functionalized by a functionality which can react with the at least one functional moiety that is carried on said silicone by forming a covalent bond; such usual reaction may be exemplified by a hydrosylilation reaction between $\equiv$Si—H moieties and $CH_2$=CH— vinyl moieties, or by the reaction occurring between thio-functional SH moieties with such vinyl moieties.

Examples of polymers having a polysiloxane backbone grafted with non-silicone organic monomers that are useful for implementing the present disclosure, as well as their particular preparation mode, are described, for example, in European Patent Application No. 0 582 152, and International Patent Application Publication Nos. WO 93/23009 and WO 95/03776, the contents of which are incorporated herein by reference.

According to one embodiment of the present disclosure, the silicone polymer having a polysiloxane backbone grafted with non-silicone organic monomers as implemented comprises the free-radical copolymerization result between, on the one hand, at least one ethylenically unsaturated non-silicone, anionic, organic monomer, and/or an ethylenically unsaturated non-silicone hydrophobic, organic monomer, and on the other hand, a silicone comprising in its chain at least one functional moiety that can react on said ethylene unsaturations of said non-silicone monomers by forming a covalent bond, for example, thio-functional moieties.

According to the present disclosure, said ethylenically unsaturated anionic monomers may be chosen, alone or as a mixture, from unsaturated, linear or branched carboxylic acids that are optionally partly or fully neutralized as a salt, these unsaturated carboxylic acids being chosen, for example, from acrylic acid, methacrylic acid, maleic acid, maleic anhydride, itaconic acid, fumaric acid, and crotonic acid. Suitable salts include, for instance, alkaline metal salts, earth-metal salts, and ammonium salts. It is to be understood that in the final silicone graft polymer, the anionic organic moiety comprising the result from the free-radical (homo) polymerization of at least one anionic monomer of the unsaturated carboxylic acid type may be post neutralized after the reaction with a base (for example, soda, ammonia, and the like) to be converted as a salt.

According to the present disclosure, ethylenically unsaturated hydrophobic monomers may be chosen, alone or as a mixture, from acrylic acid esters of alkanols and/or methacrylic acid esters of alkanols. Suitable alkanols may include, for example, those comprising from 1 to 18, for instance, from 1 to 12 carbon atoms. Non-limiting examples of monomers include isooctyl(meth)acrylate, isononyl(meth)acrylate, 2-ethylhexyl(meth)acrylate, lauryl(meth)acrylate, isopentyl(meth)acrylate, n-butyl (meth)acrylate, isobutyl(meth)acrylate, methyl(meth)acrylate, tert-butyl(meth)acrylate, tridecyl(meth)acrylate, stearyl(meth)acrylate, and mixtures thereof.

Another silicone polymer family with a polysiloxane backbone grafted with non-silicone organic monomers that is suitable for use in accordance with the present disclosure includes silicone polymers comprising within their structure at least one unit of formula (VII):

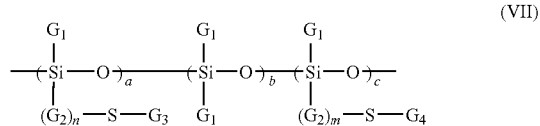
(VII)

wherein
$G_1$ radicals, which may be identical or different, are chosen from hydrogen, $C_1$-$C_{10}$ alkyl radicals, and phenyl radicals;
$G_2$ radicals, which may be identical or different, are chosen from $C_1$-$C_{10}$ alkyl radicals;
$G_3$ is a polymer radical resulting from the (homo)polymerization of at least one ethylenically unsaturated anionic monomer;
$G_4$ is a polymer radical resulting from the (homo) polymerization of at least one ethylenically unsaturated hydrophobic monomer;
m is equal to 0 or 1;
n is equal to 0 or 1;
a is an integer ranging from 0 to 50;
b is an integer that may range from 10 to 350; and
c is an integer ranging from 0 to 50;

with the proviso that a and c are not both equal to 0.

In one embodiment, the unit of formula (VII) has at least one or, in another embodiment, all of, the following characteristic features:
$G_1$ radicals are chosen from alkyl radicals, for example, methyl;
n is not equal to 0 and $G_2$ radicals are chosen from $C_1$-$C_3$ divalent radicals, for example, propylene;
$G_3$ is a polymer radical resulting from the (homo)polymerization of at least one monomer of the ethylenically unsaturated carboxylic acid type, for example, acrylic acid and/or methacrylic acid;
$G_4$ is a polymer radical resulting from the (homo)polymerization of at least one monomer of the $C_1$-$C_{10}$ alkyl methacrylate type, for example, isobutyl or methyl (meth)acrylate.

Examples of graft silicone polymers comprising at least one unit of formula (VII) include, but are not limited to, polydimethyl siloxanes (PDMS) on which mixed polymer units of the poly(meth)acrylic acid type and of the methyl poly(meth)acrylate type are grafted through a binding chain member of the thiopropylene type.

In at least one embodiment, the number molecular weight of silicone polymers having a polysiloxane backbone grafted with non-silicone organic monomers of the present disclosure may range from 10 000 to 1 000 000, for example, from 10 000 to 100 000.

Graft silicone polymers that may be used in accordance with the present disclosure include the product marketed by 3M under the trade name VS80.

H) Anionic Polyurethanes.

Polyurethanes that may be used in accordance with the present disclosure may have a basic repeating unit of formula (VII):

—X'—B—X'—CO—NH—R—NH—CO— (VIII)

wherein
X', which may be identical or different, are independently chosen from O and NH,
B is chosen from substituted or unsubstituted, divalent hydrocarbon radicals, and
R is a divalent radical chosen from branched and unbranched, alkylene radicals, of $C_6$-$C_{20}$ aromatic type, $C_1$-$C_{20}$ aliphatic type, for example, $C_1$-$C_6$, $C_1$-$C_{20}$ cycloaliphatic type, for example, $C_1$-$C_6$, these radicals being unsubstituted or substituted by at least one moiety chosen from halogen, $C_1$-$C_4$ alkoxy, and $C_6$-$C_{30}$ aryl, for example, phenyl, moieties.

In one embodiment, radical B is chosen from $C_1$-$C_{30}$ divalent radicals, for example, $C_2$-$C_{10}$ divalent radicals, and carries a moiety comprising at least one functionality chosen from carboxylic and sulfonic functionalities, said at least one functionality being in the free form or being partly or fully neutralized by means of a mineral or organic base such as alkaline metal hydroxides, alkaline earth metal hydroxides, ammonia, alkyl amines, alkanol amines, and organic aminoacids. In another embodiment, B may be the divalent radical derived from dimethylol propionic acid.

The radical R may be chosen, for example, from radicals of the following formulas:

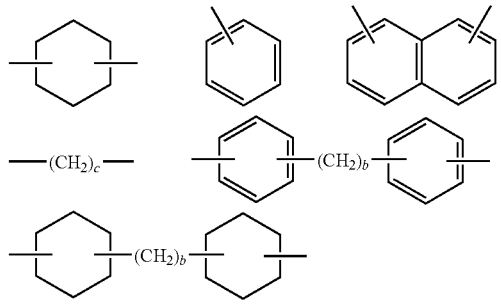

wherein b is an integer ranging from 0 to 3 and c is an integer ranging from 1 to 20, for example, from 2 to 12.

In one embodiment, the radical R may be chosen from hexamethylene, 4,4'-biphenylene methane, 2,4 and/or 2,6-tolylene, 1,5-naphthylene, p-phenylene, methylene-4,4bis-cyclohexyl radicals, and the divalent radical derived from isophorone.

According to one aspect of the present disclosure, fixing polyurethanes may comprise silicone grafts and hydrocarbon graft silicones.

Moreover, in another embodiment, a polyurethane in accordance with the present disclosure may comprise at least one polysiloxane sequence, which basic repeating unit has, for example, the following formula (IX):

—X'—P—X'—CO—NH—R—NH—CO— (IX)

wherein:
P is a polysiloxane segment,
X', which may be identical or different, are independently chosen from O and NH, and
R is a divalent radical chosen from branched and unbranched, alkylene radicals, of $C_6$-$C_{20}$ aromatic type, of $C_1$-$C_{20}$ aliphatic type, for example, $C_1$-$C_6$, of $C_1$-$C_{20}$ cycloaliphatic type, for example, $C_1$-$C_6$, these radicals being unsubstituted or substituted by at least one moiety chosen from halogen, $C_1$-$C_4$ alkoxy, and $C_1$-$C_{30}$ aryl, for example, phenyl, moieties.

In at least one embodiment, the radical R may be chosen from radicals of the following formulas:

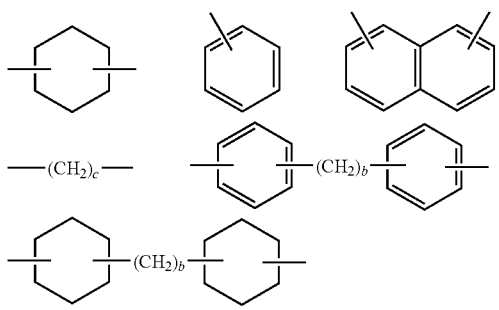

wherein b is an integer ranging from 0 to 3 and c is an integer ranging from 1 to 20, for example, from 2 to 12.

In one embodiment, the radical R may be chosen from hexamethylene, 4,4'-biphenylene methane, 2,4 and/or 2,6-tolylene, 1,5-naphthylene, p-phenylene, methylene-4,4bis-cyclohexyl radicals, and the divalent radical derived from isophorone.

The polysiloxane segment P, in at least one embodiment, may be chosen from those of formula (X):

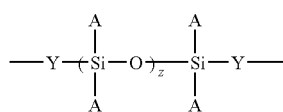

wherein:
groups A, which may be identical or different, are chosen from $C_1$-$C_{20}$ monovalent hydrocarbon groups, substantially free from any ethylenic unsaturation, and from aromatic groups,
Y is a divalent hydrocarbon group, and
Z is an integer chosen such that the polysiloxane segment mean molecular weight ranges from 300 to 10 000.

In one embodiment, divalent group Y may be chosen from alkylene groups of formula —$(CH_2)_a$—, wherein a is an integer ranging from 1 to 10.

Groups A may be chosen from $C_1$-$C_{18}$ alkyl groups, for example, methyl, ethyl, propyl, isopropyl, butyl, pentyl, hexyl, octyl, decyl, dodecyl, and octadecyl groups; cycloalkyl groups, for example, cyclohexyl; aryl groups, for example, phenyl and naphthyl groups; arylalkyl groups, for example, benzyl and phenyl ethyl; tolyl groups; and xylyl groups.

Examples of suitable fixing polyurethanes include, but are not limited to, the copolymer of dimethylol propionic acid/diisocyanate isophorone/neopentyl glycol/polyester diols (also known under the INCI name polyurethane-1) sold under the trade name Luviset® PUR by BASF, and the copolymer of dimethylol propionic acid/diisocyanate isophorone/neopentyl glycol/polyester diols/silicone diamine (also known under the INCI name polyurethane-6) sold under the trade name Luviset® Si PUR A by BASF.

Elastomeric anionic polyurethanes may also be used, such as AVALURE UR450, marketed by NOVEON.

According to one embodiment of the present disclosure, anionic polymers may be chosen from
  acrylic acid copolymers such as the terpolymer of acrylic acid/ethyl acrylate/N-tert-butyl acrylamide sold under the trade name ULTRAHOLD STRONG® by BASF,
  copolymers of methacrylic acid and ethyl acrylate, for example, in aqueous dispersion, such as LUVIFLEX SOFT and LUVIMER MAE marketed by BASF,
  copolymers derived from crotonic acid, such as terpolymers of vinyl acetate/vinyl tert-butyl benzoate/crotonic acid, as well as terpolymers of crotonic acid/vinyl acetate/vinyl neododecanoate sold, for example, under the trade name Resin 28-29-30 by NATIONAL STARCH,
  polymers derived from maleic, fumaric, and itaconic acids and anhydrides with vinyl esters, vinyl ethers, vinyl halides, phenyl vinyl derivatives, acrylic acid and esters thereof such as the copolymer of methylvinyl ether and monoesterified maleic anhydride sold under the trade name GANTREZ®ES 425 by ISP, LUVISET SI PUR, MEXOMERE PW,
  elastomeric or non-elastomeric anionic polyurethanes,
  sulfoisophthalate moiety polymers,
  anionic silicone graft polymers, such as the product with trade name VS80, and
  copolymers of methacrylic acid and acrylic acid/ethyl acrylate/methyl methacrylate, for example, AMERHOLD DR25.

Amphoteric Fixing Polymers

Amphoteric polymers that may be used in accordance with the present disclosure may be chosen from polymers having units B and C statistically distributed within the polymer chain, where B is a unit derived from a monomer comprising at least one basic nitrogen atom and C is a unit derived from an acidic monomer comprising at least one moiety chosen from carboxylic and sulfonic moities, or B and C may represent moieties derived from zwitterionic monomers of carboxybetaines or sulfobetaines; B and C may also represent a cationic polymer chain comprising primary, secondary, tertiary, and/or quaternary amine moieties, where at least one of the amine moieties carries a carboxylic or sulfonic moiety bound through a hydrocarbon group, or B and C may form part of a chain of an ethylene-dicarboxylic unit containing polymer, one of the carboxylic moieties of which has been caused to react with a polyamine comprising at least one moiety chosen from primary and secondary amine moieties.

Suitable amphoteric polymers may be chosen, for example from:
  1) polymers resulting from the copolymerization of a monomer derived from a vinyl compound carrying a carboxylic moiety, such as acrylic acid, methacrylic acid, maleic acid, and α-chloracrylic acid, and from a basic monomer derived from a substituted vinyl compound comprising at least one basic atom such as dialkylaminoalkyl methacrylate and -acrylate, and dialkylaminoalkyl methacrylamide and -acrylamide. Such compounds are described, for example, in U.S. Pat. No. 3,836,537.

Such a vinyl compound may also, in one embodiment, be a dialkyldiallyl-ammonium salt such as diethyldiallyl-ammonium chloride.

2) polymers comprising units derived from:
a) at least one monomer chosen from acrylamides and methacrylamides, substituted on the nitrogen by an alkyl group,
b) at least one acidic comonomer comprising at least one reactive carboxylic moiety, and
c) at least one basic comonomer, such as primary, secondary, tertiary and quaternary amine substituted esters of acrylic and methacrylic acids, and the quaternization product of dimethyl aminoethyl methacrylate with dimethyl or diethyl sulfate.

Examples of suitable N-substituted acrylamides and methacrylamides according to the present disclosure include moieties, the alkyl groups of which comprise from 2 to 12 carbon atoms, for example, N-ethyl acrylamide, N-tert-butyl acrylamide, N-tert-octyl acrylamide, N-octyl acrylamide, N-decyl acrylamide, N-dodecyl acrylamide, and the corresponding methacrylamides.

Acidic comonomers may be chosen from acrylic, methacrylic, crotonic, itaconic, maleic, and fumaric acids, and alkyl monoesters comprising from 1 to 4 carbon atoms of maleic or fumaric acids or anhydrides. Suitable basic comonomers include aminoethyl, butylaminoethyl, N,N'-dimethylaminoethyl, and N-tert-butylaminoethyl methacrylates. Copolymers having the CTFA name (4$^{th}$ ed. 1991) octylacryl amide/acrylates/butylaminoethyl methacrylate copolymer, such as the products sold under the trade name AMPHOMER® and LOVOCRYL® 47 by NATIONAL STARCH are also suitable for use.

3) crosslinked and partly or fully alkylated polyaminoamides derived from polyaminoamides of formula (XI):

$$-[CO-R_4-CO-Z]-\quad\quad(XI)$$

wherein
$R_4$ is a divalent group derived from a saturated dicarboxylic acid, from an ethylene double bond containing, aliphatic, mono or -dicarboxylic acids, from an ester of a lower alkanol comprising from 1 to 6 carbon atoms of these acids, and/or from a group resulting from the addition of any one of said acids with a bis-primary or bis-secondary derived amine, and
Z is chosen from polyalkylene-bis-primary, mono- or bis-secondary polyamine groups, comprising, for example:
a) in an amount ranging from 60 to 100% by mol, the group of formula (XII):

$$-NH-[(CH_2)_x-NH]_p-\quad\quad(XII)$$

wherein x is 2 and p is 2 or 3, or alternatively, x is 3 and p is 2, this group being derived from diethylene triamine, triethylene tetraamine, and/or dipropylene triamine;
b) in an amount ranging from 0 to 40% by mol, the above group (XII), wherein x is 2 and p is 1, being derived from ethylene diamine, or the group derived from piperazine

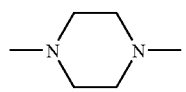

c) in an amount ranging from 0 to 20% by mol, the —NH—(CH$_2$)$_6$—NH group derived from hexamethylene diamine, these polyaminoamines being crosslinked by adding a difunctional crosslinking agent chosen from epihalohydrines, diepoxies, dianhydrides, and unsaturated bis-derivatives, by means of 0.025 to 0.35 mol of a crosslinking agent per amine moiety of the polyaminoamide and alkylated by the action of acrylic acid, chloracetic acid or by means of an alkane-sultone, or their salts.

Saturated carboxylic acids may be chosen from acids of 6 to 10 carbon atoms, such as adipic acid, 2,2,4-trimethyl adipic acid, and 2,4,4-trimethyl adipic acid, terephthalic acid, ethylene double-bond acids such as for acrylic, methacrylic, and itaconic acids. Alkane sultones used for the alkylation may, for example, be propane or butane sultone, and alkylating agent salts may, for example, be sodium and potassium salts.

4) Polymers comprising zwitterionic units of formula (XIII):

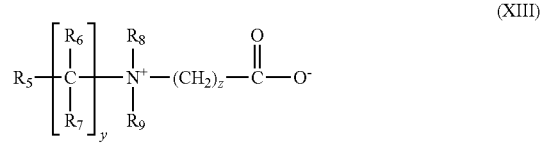

wherein
$R_5$ is a polymerizable unsaturated moiety such as an acrylate, methacrylate, acrylamide or methacrylamide moiety,
y and z, which may be identical or different, are integers ranging from 1 to 3,
$R_6$ and $R_7$, which may be identical or different, are chosen from hydrogen, and methyl, ethyl, and propyl moieties,
$R_8$ and $R_9$, which may be identical or different, are chosen from hydrogen and alkyl groups such that the sum of the carbon atoms contained in $R_8$ and $R_9$ does not exceed 10.

Polymers comprising such units may also comprise units derived from non zwitterionic monomers, such as dimethyl- or diethylaminoethyl acrylate and methacrylate, alkyl acrylates and methacrylates, acrylamides and methacrylamides, and vinyl acetate.

5) Chitosan derived polymers comprising monomer units chosen from units of formulas (XIV)-(XVI):

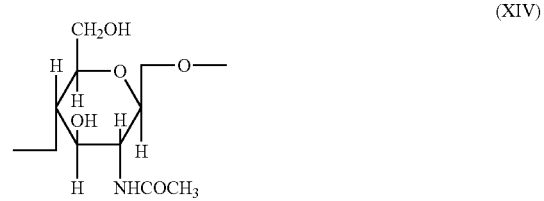

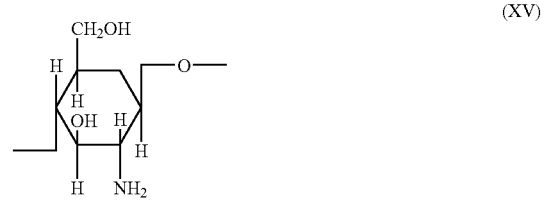

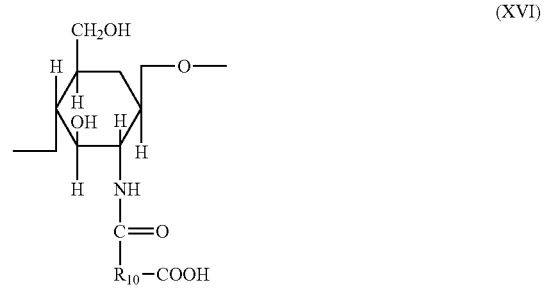

wherein
the units of formula (XIV) may be present in an amount ranging from 0 to 30%,
the units of formula (XV) may be present in an amount ranging from 5 to 50%, and
the units of formula (XVI) may be present in an amount ranging from 30 to 90%, wherein $R_{10}$ is a group of formula (XVII):

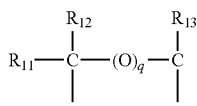

(XVII)

wherein
q is equal to 0 or 1;
when q is 0, $R_{11}$, $R_{12}$, and $R_{13}$, which may be identical or different, are independently chosen from hydrogen; methyl, hydroxyl, acetoxy, and amino radicals; monoalkyl amine radicals and dialkyl amine radicals optionally interrupted with at least one nitrogen atom and/or optionally substituted with at least one group chosen from amine, hydroxyl, carboxyl, alkylthio, and sulfonic groups; and alkylthio radicals, the alkyl group of which carries an amino radical, wherein at least one of the $R_{11}$, $R_{12}$, or $R_{13}$ groups is a hydrogen atom; and
when q is 1, $R_{11}$, $R_{12}$, and $R_{13}$ are each hydrogen atoms, as well as the acid and base addition salts of these compounds.
6) Polymers derived from the N-carboxyalkylation of chitosan.
7) Polymers of formula (XVIII) described, for example, in French Patent No. 1°400°366:

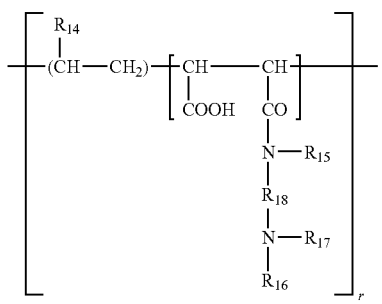

(XVIII)

wherein
r is an integer greater than 1,
$R_{14}$ is chosen from hydrogen, $CH_3O$, $CH_3CH_2O$, and phenyl,
$R_{15}$ is chosen from hydrogen and lower alkyl groups such as methyl and ethyl,
$R_{16}$ is chosen from hydrogen and lower alkyl groups such as methyl and ethyl,
$R_{17}$ is chosen from lower alkyl groups such as methyl and ethyl, and $-R_{18}-N(R_{16})_2$ groups, wherein $R_{18}$ is chosen from $-CH_2CH_2-$, $-CH_2CH_2-CH_2-$, and $-CH_2CH(CH_3)-$ moieties, and $R_{16}$ is defined above,
as well as higher homologs of these groups comprising up to 6 carbon atoms.

8) Amphoteric polymers of the -D-X-D-X type, chosen from:
a) polymers obtained from the action of chloracetic acid or sodium chloracetate on compounds comprising at least one unit of formula (XIX):

-D-X-D-X-D- (XIX)

wherein D is

and
X is chosen from the symbols E and E', wherein E and E', which may be identical or different, are chosen from divalent groups which are linear chain or branched alkylene groups comprising up to 7 carbon atoms in the main chain which may be unsubstituted or substituted with hydroxyl moieties, and which may comprise oxygen, nitrogen, and/or sulfur atoms, from 1 to 3 aromatic and/or heterocyclic rings; the oxygen, nitrogen, and/or sulfur atoms being present in the form of ether, thioether, sulfoxide, sulfone, sulfonium, alkyl amine, alkenyl amine, hydroxyl, benzyl amine, amine oxide, quaternary ammonium, amide, imide, alcohol, ester, and/or urethane moieties.
b) Polymers of formula (XX):

-D-X-D-X— (XX)

wherein D is

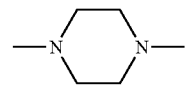

and X is chosen from the symbol E and E', and at least once X is E', wherein E is defined above and E' is a divalent group which is a linear chain or branched alkylene group comprising up to 7 carbon atoms in the main chain which may be unsubstituted or substituted with at least one hydroxyl group, and comprising at least one nitrogen atom, the nitrogen atom being substituted with an alkyl chain optionally interrupted with an oxygen atom and comprising at least one functionality chosen from carboxyl and hydroxyl functionalities, betainized by reaction with chloracetic acid or sodium chloracetate.
9) Copolymers of $(C_1-C_5)$alkyl vinyl ether/maleic anhydride partly modified by half-amidification with a N,N-dialkylaminoalkyl amine such as N,N-dimethylaminopropyl amine or by half-esterification with a N,N-dialkanol amine. These copolymers may also include other vinyl comonomers such as vinyl caprolactame.
According to one embodiment of the present disclosure, fixing amphoteric polymers that may be used in accordance with the present disclosure may be chosen from branched, block copolymers comprising:
(a) non ionic units derived from at least one monomer chosen from $C_1-C_{20}$ alkyl (meth)acrylates, N-mono($C_2$-$C_{12}$ alkyl)(meth)acrylamides, and N,N-di($C_2$-$C_{12}$ alkyl) (meth)acrylamide,
(b) anionic units derived from at least one monomer chosen from acrylic acid and methacrylic acid, and (c) polyfunctional units derived from at least one monomer comprising at least two polymerizable unsaturated functional groups and having a structure, for example, made of hydrophobic blocks onto which several more hydrophilic blocks are bound through polyfunctional units (c).

The amphoteric polymers may, for example, have at least two glass transition temperatures (Tg), one which at least is higher than 20° C. and the other being lower than 20° C.

Non-limiting examples of amphoteric polymers include polymers comprising units derived from:
  (a) at least one monomer chosen from acrylamides and methacrylamides substituted on the nitrogen with an alkyl group,
  (b) at least one acidic comonomer comprising at least one reactive carboxylic moiety, and
  (c) at least one basic comonomer such as primary, secondary, tertiary, and quaternary amine substituted esters of the methacrylic and acrylic acids, and the quaternization product of dimethylaminoethyl methacrylate with dimethyl or diethyl sulfate.

Examples of suitable commercial products include the polymers sold under the trade name AMPHOMER by NATIONAL STARCH.

The at least one fixing polymer chosen from anionic and amphoteric fixing polymers may be present in the first composition in an amount ranging from 0.1 to 50%, for example, from 1 to 30% by weight, relative to the total weight of the first composition.

Second Composition

As discussed above, a second composition is applied to the hair, prior to or after applying the first composition comprising at least one solubilized fixing polymer.

The second composition comprises, in a cosmetically acceptable medium, at least one acid chosen from mineral and organic acids.

Mineral and Organic Acids

Suitable organic acids may be chosen from acids comprising at least one functionality chosen from carboxylic, sulfonic, phosphonic, and phosphoric acid functionalities. The organic acids may comprise other chemical functionalities, for example, hydroxy and amino functionalities. The organic acids may be saturated or unsaturated.

Non-limiting examples of organic acids include acetic acid, propanoic acid, butanoic acid, lactic acid, glycolic acid, ascorbic acid, maleic acid, phthalic acid, succinic acid, taurine acid, and citric acid.

In at least one embodiment, the organic acid may be citric acid.

Mineral acids may be chosen from monoacidic and polyacidic acids.

Examples of mineral acids include, but are not limited to, hydrochloric acid, orthophosphoric acid, sulfuric acid, and boric acid.

The at least one acid chosen from mineral and organic acids may be present in the second composition ranging from 0.15 to 10%, for example, from 1 to 10% by weight, relative to the total weight of the second composition.

As discussed above, the at least one fixing polymer and the at least one acid are respectively present in the first and second composition, each in cosmetically acceptable mediums.

The cosmetically acceptable medium for the first and the second composition may be chosen from water, $C_1$-$C_6$ alcohols, for example, alkanols such as ethanol, propanol, and isopropanol, alkane diols such as ethylene glycol, propylene glycol, and pentane diol, benzyl alcohol, $C_5$-$C_{10}$ alkanes, acetone, methylethyl ketone, methyl acetate, butyl acetate, ethyl acetate, dimethoxyethane, diethoxyethane, and mixtures thereof.

The first and/or the second composition may further comprise conventional cosmetic additives chosen, for example, from thickeners, softeners, antifoaming agents, sunscreens, moisturizing agents, dyes, pigments, fragrances, preserving agents, anionic, cationic, non ionic surfactants, amphoteric surfactants, non-fixing polymers, volatile silicones, non-volatile silicones, vegetable oils, animal oils, mineral oils, and synthetic oils, proteins, vitamins, polyols, and mixtures thereof.

The first composition and the second composition may be homogenous solutions, suspensions, water-in-oil emulsions, oil-in-water emulsions, or multiple emulsions, all of them having a fluid consistency, that has been at least partially thickened or gelled.

The pH value of the first composition may range from 4 to 10, for example, from 6 to 10.

The pH value of the second composition may range from 1 to 7, for example, from 1.5 to 5.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLE

The method of the present disclosure is implemented by using a first composition and a second composition.

The first and the second compositions have the following formulations:

First Composition:

| | |
|---|---|
| LUVIFLEX SOFT (methacrylic acid/ethyl acrylate copolymer, 50/50 in aqueous dispersion) | 50 g |
| 2-amino-2-methyl-1-propanol | qs pH 6 |
| Demineralized water | qs 100 g, pH 6 |

Second Composition:

| | |
|---|---|
| Citric acid | 3 g |
| Demineralized water | qs 100 g, pH 2.2 |

The first composition was applied to a sample of hair. The hair was then shaped by hand. The second composition was then applied and left on for five minutes at room temperature. The hair was then rinsed.

The hair treated according to the present disclosure had a very satisfactory hair styling hold, that was resistant to shampoos. The hair was soft and felt very natural.

What is claimed is:

1. A semi permanent hair shaping method comprising:
   (a) applying to the hair a first composition consisting, in a cosmetically acceptable medium, an anionic polymer, wherein the anionic polymer is 50/50 methacrylic acid/ethyl acrylate block copolymer, this application optionally being followed by a resting time for said first composition, wherein the anionic polymer is present in the first composition in an amount ranging from 0.1 to 50% by weight, relative to the total weight of the first composition, wherein the pH value of the first composition ranges from 6 to 10,
   (b) applying to the hair a second composition consisting, in a cosmetically acceptable medium, an acid wherein the acid is citric acid, such application optionally being followed by a resting time for said second composition, wherein step b) is conducted after step a), wherein the acid is present in the second composition in an amount ranging from 0.15 to 10% by weight, relative to the total weight of second composition, and wherein the pH value of the second composition ranges from 1.5 to 5,
   (c) rinsing the hair, and
   (d) shaping the hair either after applying the first composition of step a), or after applying the second composition of step b) and prior to the rinsing step c),
   wherein the semi permanent hair shaping method produces a hair shape permanent with respect to at least one shampoo, wherein the method does not comprise either opening the hair keratin disulfide bonds with a reducing composition or re-forming said disulfide bonds with an oxidizing composition.

2. The method of claim 1, wherein the at least one anionic polymer is present in the first composition in an amount ranging from 1 to 30% by weight, relative to the total weight of the first composition.

3. The method of claim 1, wherein the at least one acid is present in the second composition in an amount ranging from 1 to 5% by weight, relative to the total weight of second composition.

* * * * *